United States Patent
Gluck et al.

[11] Patent Number: 5,424,649
[45] Date of Patent: Jun. 13, 1995

[54] SOIL MOISTURE SENSOR

[75] Inventors: Israel Gluck; Anatoly Friedman; Naftali Feniger, all of Ashrat, Israel

[73] Assignee: Silora Television & Electronics, Ashrat, Israel

[21] Appl. No.: 181,220

[22] Filed: Jan. 13, 1994

[30] Foreign Application Priority Data

Aug. 29, 1993 [IL] Israel ................................. 106829

[51] Int. Cl.$^6$ ............................................. G01R 27/26
[52] U.S. Cl. .................................. 324/667; 324/690; 137/78.5
[58] Field of Search .............. 137/78.5; 324/667, 689, 324/690; 361/181, 178; 73/335.03, 335.04–335.05

[56] References Cited

U.S. PATENT DOCUMENTS

| | | | |
|---|---|---|---|
| 4,137,931 | 2/1979 | Hasenbeck | 137/78.3 |
| 4,850,386 | 7/1989 | Bireley | 324/667 |
| 4,952,868 | 8/1990 | Schrer, III | 137/78.3 |
| 4,989,628 | 2/1991 | Gil et al. | 137/78.3 |
| 4,993,640 | 2/1991 | Baugh | 137/78.3 |

Primary Examiner—Maura K. Regan
Attorney, Agent, or Firm—Edward Langer

[57] ABSTRACT

A soil moisture sensor using sensor electrodes each designed with a larger capacitance for reduced sensitivity to soil resistance and increased sensitivity to soil moisture surrounding the electrode. The soil moisture sensor is provided as a pair of cylindrical rods each coated with a thin layer of dielectric material, which are buried in the soil or other medium and are connected to a conversion circuit in which the electrodes act as a variable capacitance. The capacitance developed by each of the sensor electrodes is related to the moisture contained in the soil particles surrounding the electrodes. An effective conducting area is developed by the soil particles in contact with the electrodes and this determines the value of the variable capacitance presented to the conversion circuit. The conversion circuit is a multivibrator in which the variable capacitance determines the output frequency, and this provides a measurement of soil moisture. Alternatively, the conversion circuit provides the measurement as a voltage output. The use of a relatively thin dielectric coating on each of the electrodes increases the capacitance and reduces the soil resistance as a factor in the soil moisture measurement. Based on the cylindrical shape of the sensor electrodes and dielectric coating, a linear relationship is developed between capacitance and the electrode length in contact with soil particles containing moisture, which increases the accuracy of soil moisture measurement at soil depths of interest. The inventive soil moisture sensor can be used to control valves in automatically-controlled irrigation systems.

18 Claims, 12 Drawing Sheets

SOIL MOISTURE SENSOR

FIELD OF THE INVENTION

The present invention relates to soil moisture sensors, and more particularly, to a soil moisture sensor which measures the freely available moisture in the soil surrounding the sensor, to provide increased accuracy of control for irrigation systems.

BACKGROUND OF THE INVENTION

The prior art contains several soil moisture sensor designs, each of which attempts to measure soil moisture by electronic means based on the capacitance effect between sensor plates.

A variation of these designs is given in U.S. Pat. No. 4,850,386 to Bireley, which discloses two electrodes and a detector circuit connected to the electrodes to measure the impedance between them. At least one of the electrodes has a relatively thick dielectric coating, so that the sensor reactance is also relatively high. The water droplets in the soil form paths to the dielectric coating between the electrodes, which are preferably situated relatively closely together, to reduce the resistance and minimize the capacitative effect. The impedance between the electrodes varies with the moisture level of the soil, but since the design features a small capacitance, the measurement is not as sensitive to changes in moisture.

In U.S. Pat. No. 4,837,499 to Scherer there is disclosed a soil moisture sensor having a pair of concentrically disposed cylindrical conductors separated by a fibrous material, to form a capacitor whose resistance varies with the moisture level.

In U.S. Pat. No. 4,683,904 to Iltis, there is disclosed a moisture Sensor having an oscillator which changes its frequency as the capacitance between a pair of plates changes due to the moisture between them. The sensor responds to soil moisture changes as a function of the change in the dielectric constant.

In U.S. Pat. No. 4,540,936 to Walsh, there is disclosed a soil moisture sensor provided as a pair of coaxial tubes forming a coaxial capacitor, which can be inserted into the soil. The coaxial capacitor is connected in a Wien bridge circuit for measuring the impedance by application of a variable frequency oscillator and frequency detector, and once the resonant frequency is detected, the capacitance can be derived along with the dielectric constant and soil moisture.

U.S. Pat. No. 3,771,548 to Rauchwerger discloses a variable capacitor provided as two plates between which the moisture is directly proportional to the capacitance between them. An oscillator is used to develop a voltage across the capacitor which is measured by a peak voltage detector, and from this the capacitance is derived and the also the soil moisture, which is directly proportional to the capacitance.

Still another moisture sensor is described in U.S. Pat. No. 3,626,286 to Rauchwerger, in which two plates are separated by the soil, and the conductive moisture of the soil affects the capacitance which is measured between the plates. One of the problems with this type of sensor is that the soil itself is used as the dielectric material, and thus the soil composition is a factor which causes a variation in the performance of the sensor.

As revealed by a review of the prior art, existing techniques focus on the capacitance between two electrodes to determine the soil moisture. Typically, the capacitance has a low value, so that a small change in the capacitance is caused by a change in moisture, and therefore the oscillator frequency is low to allow for the reactance to be high relative to the soil resistance. The low frequency causes the capacitor to act as an electrolytic capacitor, which exhibits parasitic capacitance caused by ionic accumulation on the electrodes at low frequency, in the range below 30–70 kHz. The undesirable effect of parasitic capacitance causes problems in soil moisture measurement since the capacitance is not strictly dependent on the actual moisture, but is distorted by the parasitic capacitance field effects.

Another problem associated with the prior art moisture sensors is that they use metallic electrodes which are exposed to the soil, and so become oxidized, so that they lose their effectiveness, unless expensive metals are used.

As described above, the dominant resistance of the soil does not allow measurement of the freely available water or soil moisture, and thus the measurement is too easily affected by conductivity of the ground, which is a function of salinity.

Thus, it would be desirable to provide a soil moisture sensor which is less affected by soil resistance and provides a more accurate measurement of soil moisture than existing designs.

SUMMARY OF THE INVENTION

Accordingly, it is a principal object of the present invention to overcome the above-mentioned disadvantages of prior art soil moisture designs and provide a soil moisture sensor which uses sensor electrodes each designed with a larger capacitance for reduced sensitivity to soil resistance and increased sensitivity to soil moisture surrounding the electrode.

In accordance with a preferred embodiment of the present invention, there is provided a soil moisture sensor comprising:

at least two rod-shaped electrodes each disposed in the earth and having a thin dielectric coating, each said electrode defining a first plate of a capacitor, said thin dielectric coating being in contact over an area thereof with a plurality of soil particles containing moisture to define a second plate of each of said capacitors over said contact area;

variable frequency oscillator means coupled to said capacitors and providing an output frequency responsive to a sensed capacitance, wherein said sensed capacitance is related to an effective conducting area developed by said contact area of moisture contained by said plurality of soil particles.

In a preferred embodiment, the soil moisture sensor is provided as a pair of cylindrical rods each coated with a thin layer of dielectric material, which are buried in the soil or other medium and are connected to a conversion circuit in which the electrodes act as a variable capacitance. The capacitance developed by each of the sensor electrodes related to the is moisture contained in the soil particles surrounding the electrodes. Since the moisture is a conductor, an effective conducting area is developed by the soil particles containing moisture which are in contact with the electrodes, and this determines the value of the variable capacitance presented to the conversion circuit.

The soil moisture sensor can be constructed as a serial connection of two equivalent capacitances, with the conductivity of the soil containing moisture providing the serial connection. Each of the equivalent capacitances can be provided by parallel connection of a plurality of dielectric-coated electrodes, each providing a capacitor.

The conversion circuit may be a multivibrator in which the variable capacitance determines the output frequency, and this provides a measurement of soil moisture. Alternatively, the conversion circuit provides the measurement as a voltage output.

The use of a relatively thin dielectric coating on each of the electrodes increases the capacitance, which translates into a reduction in the soil resistance as a factor in the soil moisture measurement. The coated electrodes and the moisture surrounding them provides a soil moisture measurement based on the available moisture of the soil defining the effective conducting area, representing the excess water freely available for plants.

Based on the cylindrical shape of the sensor electrodes and dielectric coating, a linear relationship is developed between capacitance and the electrode length in contact with soil particles containing moisture, which increases the accuracy of soil moisture measurement at soil depths of interest.

The inventive soil moisture sensor can be used to activate a flow valve controller designed for use in automatically-controlled irrigation systems, and it can be supplied as a separate device which interfaces with an existing system, or integrated with a timer and flow valve as one unit.

Other features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENTS

Figure 1:
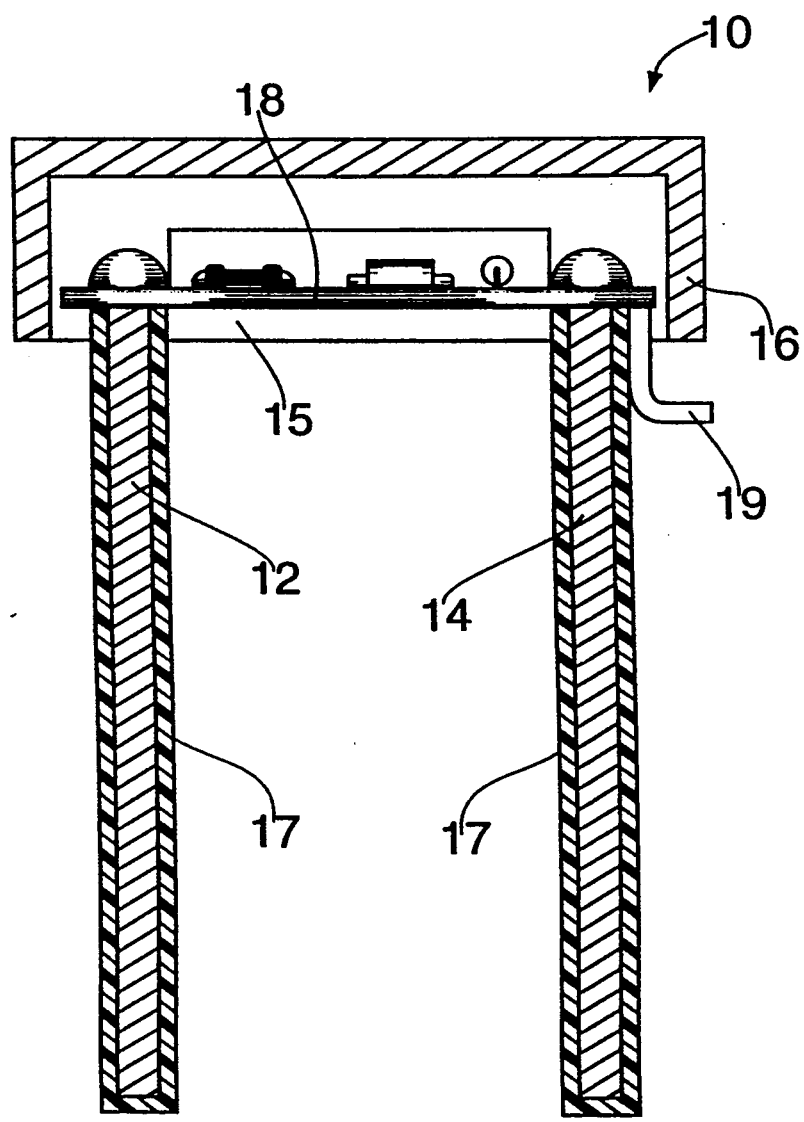
FIG. 1 is a front view of a preferred embodiment of a soil moisture sensor constructed and operated in accordance with the principles of the present invention.

Referring now to FIG. 1, there is shown a front view of a preferred embodiment of a soil moisture sensor 10 constructed and operated in accordance with the principles of the present invention. Sensor 10 comprises a pair of cylindrically-shaped electrodes 12, 14 of a predetermined length, each being anchored in a sealing material 15 like epoxy at an upper end thereof in a housing 16, with its free end extending into soil (not shown) for moisture measurement purposes. Each electrode 12, 14 is coated with a thin layer of dielectric material 17 over its length, and the electrode pair is connected to a conversion circuit 18 for soil moisture measurement, as described further herein. A cable 19 enables external connection of the output signal of sensor 10.

In accordance with the principles of the present invention, sensor 10 is designed to provide a variable capacitance to conversion circuit 18, based on the capacitance of each of electrodes 12, 14 in relation to the surrounding area of the moisture in the soil in which it is buried. The equivalent capacitance (Cs) of each capacitor provided by dielectric coating 17 on cylindrical electrodes 12, 14 can be represented by the following mathematical relationship:

$$Cs = \frac{2\pi\epsilon L}{\ln(Rout/Rin)} \qquad (1)$$

where $\epsilon$ = dielectric constant of the coating on electrodes 12, 14
L = effective length of each electrode
Rout = radius of the electrode with dielectric coating
Rin = radius of the electrode alone As can be seen from the relationship of equation 1, a relatively high capacitance can be obtained where a thin dielectric coating 17 is used, since the ratio of the denominator will be a relatively low value. Achievement of a high capacitance means the reactance will dominate the electrical characteristics of sensor 10, and the soil resistance will be less important.

For example, for a thin dielectric coating 17 of 50 microns length, a capacitance of 4 and a 100 mm rod nanofarads is developed, enabling operation of conversion circuit 18 of sensor 10 at a high frequency of several hundred kHz.

In accordance with the principles of the invention, as can be seen from equation 1, the capacitance of soil moisture sensor 10 is directly proportional to the electrode effective length, which is the length over which the dielectric coating 17 is in contact with moisture or other conducting liquid. Thus, soil moisture sensor 10 can be used as a level sensor, since it provides a capacitance related to the level of conducting liquid in contact with dielectric coating 17 over electrodes 12, 14.

Figure 3:
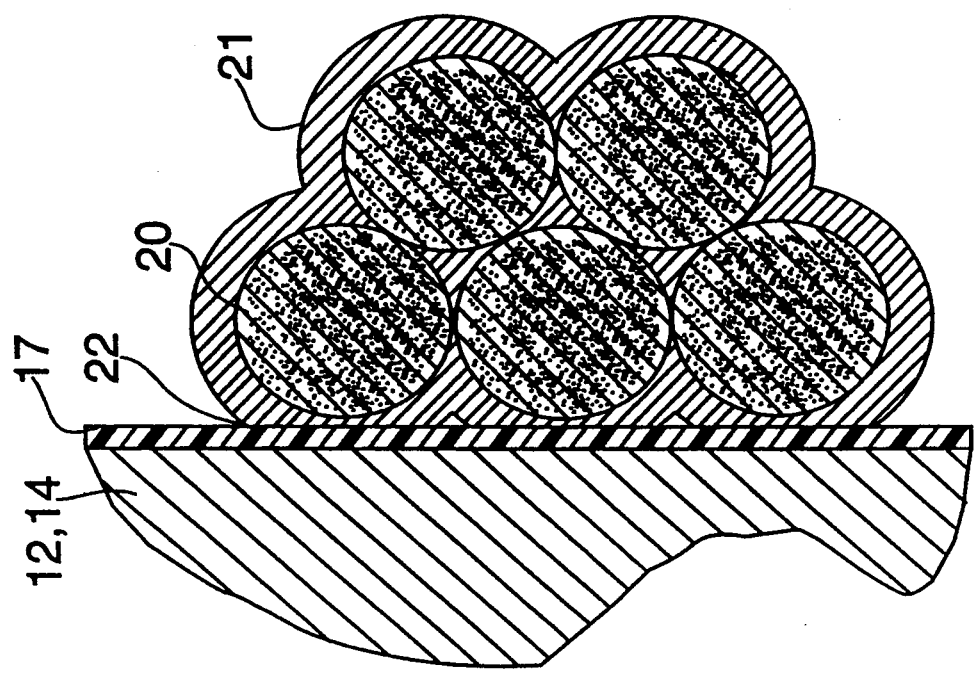
FIGS. 2-3 illustrate an electrode portion of the sensor of FIG. 1 in contact with moisture surrounding soil particles.
Figure 2:
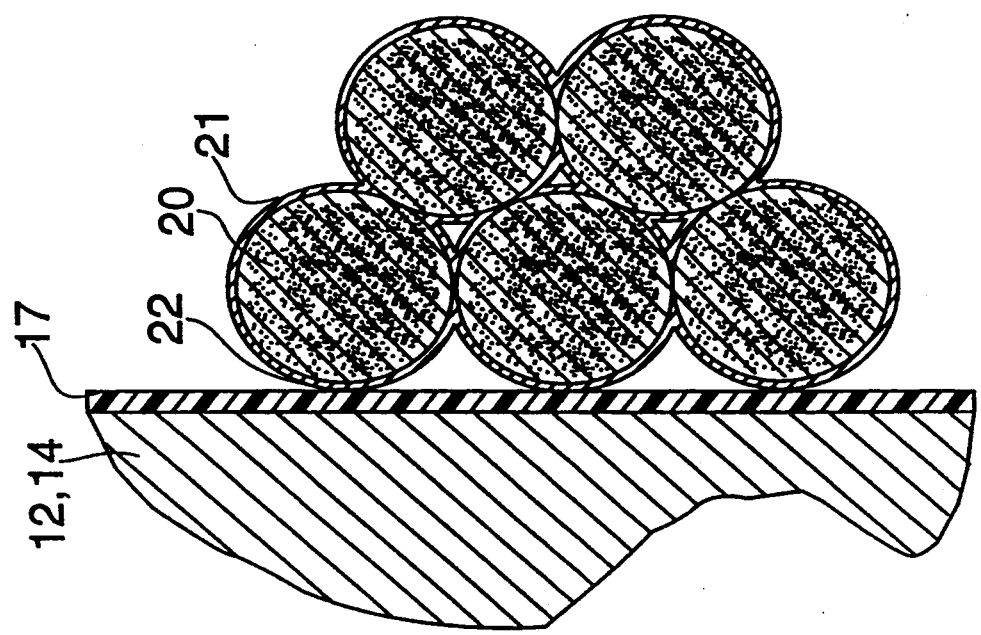

As shown by the illustrations of FIGS. 2-3, when buried in the soil, dielectric coating 17 of each of electrodes 12, 14 contacts moisture in soil particles 20 which surround the space occupied by the electrodes. These illustrations are a simplification in enlarged form of the contact surfaces between dielectric coating 17 of electrodes 12, 14 and soil particles 20, for different soil moisture conditions. The moisture contained by the soil is represented as a ring 21 having a thickness related to the quantity of water surrounding each soil particle 20, and to the surface water tension developed. The thickness of ring 21 in FIG. 2 is smaller than that in FIG. 3, such that in the FIG. 2 condition, the quantity of water present in the soil is less than that for the condition of FIG. 3.

The contact surface between ring 21 and the dielectric coating 17 on each of electrodes 12, 14 is represented by an effective conducting area 22, which in FIG. 2 is smaller than that of FIG. 3, since the quantity of water is reduced. The size of the effective conducting area 22 adjusts the variable capacitance presented by sensor 10 to the conversion circuit, and this characteristic is used for the soil moisture measurement. As suggested by the illustrations of FIGS. 2-3, the effective conducting area 22 is related to the freely available excess water surrounding soil particles 20, and so provides a good indication of the soil moisture conditions to support vegetation.

One of the major differences between the prior art and the present invention is that in the prior art, the measurement of capacitance is made between at least two electrodes, and in the invention the capacitance measurement is between each of electrodes 12, 14 and its surrounding effective conducting area. As described above with reference to FIGS. 2-3, the equivalent capacitance of sensor 10 is variable and is dependent on the effective conducting area of water in the soil around it. In addition, the capacitance is high and the reactance is the dominant characteristic, and this means that the soil resistance has less effect on impedance.

Figure 4:
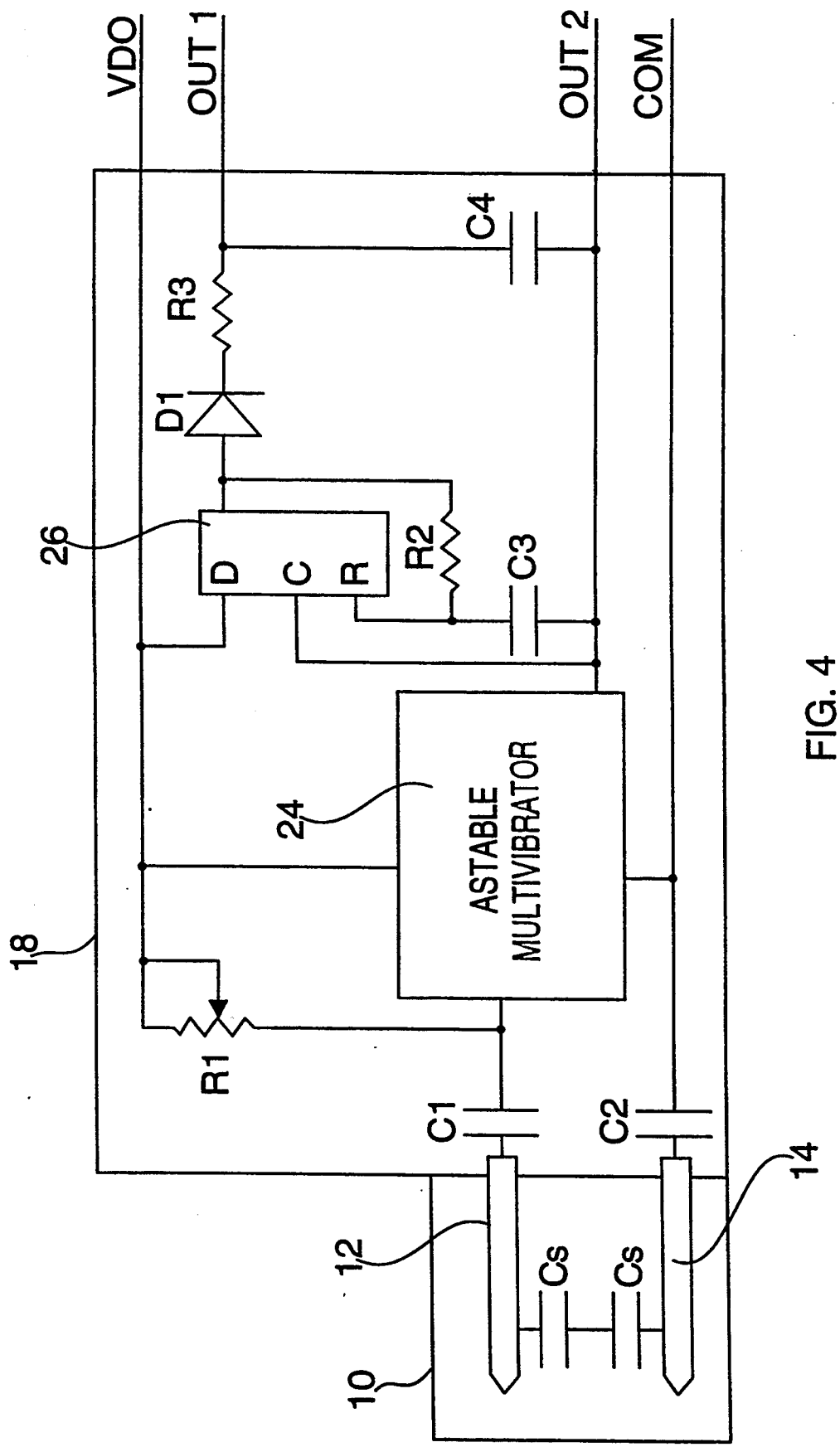
FIG. 4 is an electronic schematic diagram of a conversion circuit for making a soil moisture measurement using the sensor of FIGS. 1-3.

Referring now to FIG. 4, there is shown an electronic schematic diagram of conversion circuit 18 for making a soil moisture measurement using sensor 10 of FIGS. 1-3. The conversion circuit 18 operates based on an astable multivibrator 24, which provides an output on terminal OUT2 with a frequency based on the equivalent capacitance Cs presented to its input by sensor 10. Each of a pair of isolation capacitors C1 and C2 is connected in series with sensor electrodes 12, 14, to reduce the undesirable effects which may result from damage to dielectric coating 17 as sensor 10 is inserted into the soil.

The frequency of astable multivibrator 24 is controlled by the setting of variable resistor R1. The conversion circuit 18 also contains a frequency-to-voltage converter comprising flip-flop 26 and providing a voltage output using resistors R2-R3, diode D1 and capacitors C3 and C4.

The pulse width output from flip-flop 26 is fixed, and has a periodicity which is dependent on the frequency of the multivibrator 24 in accordance with the relation $f = 1/T$ (where f=frequency and T=period). The frequency-to-voltage conversion is performed directly by diode D1, resistor R3 and capacitor C4. Flip-flop 26 provides pulses with a fixed duration based on the values of R2 and C3, and these pulses are rectified by diode D1, such that the accumulated charge on capacitor C4 produces a voltage on output terminal OUT1 which is effectively the soil moisture expressed as a voltage.

Figure 5:
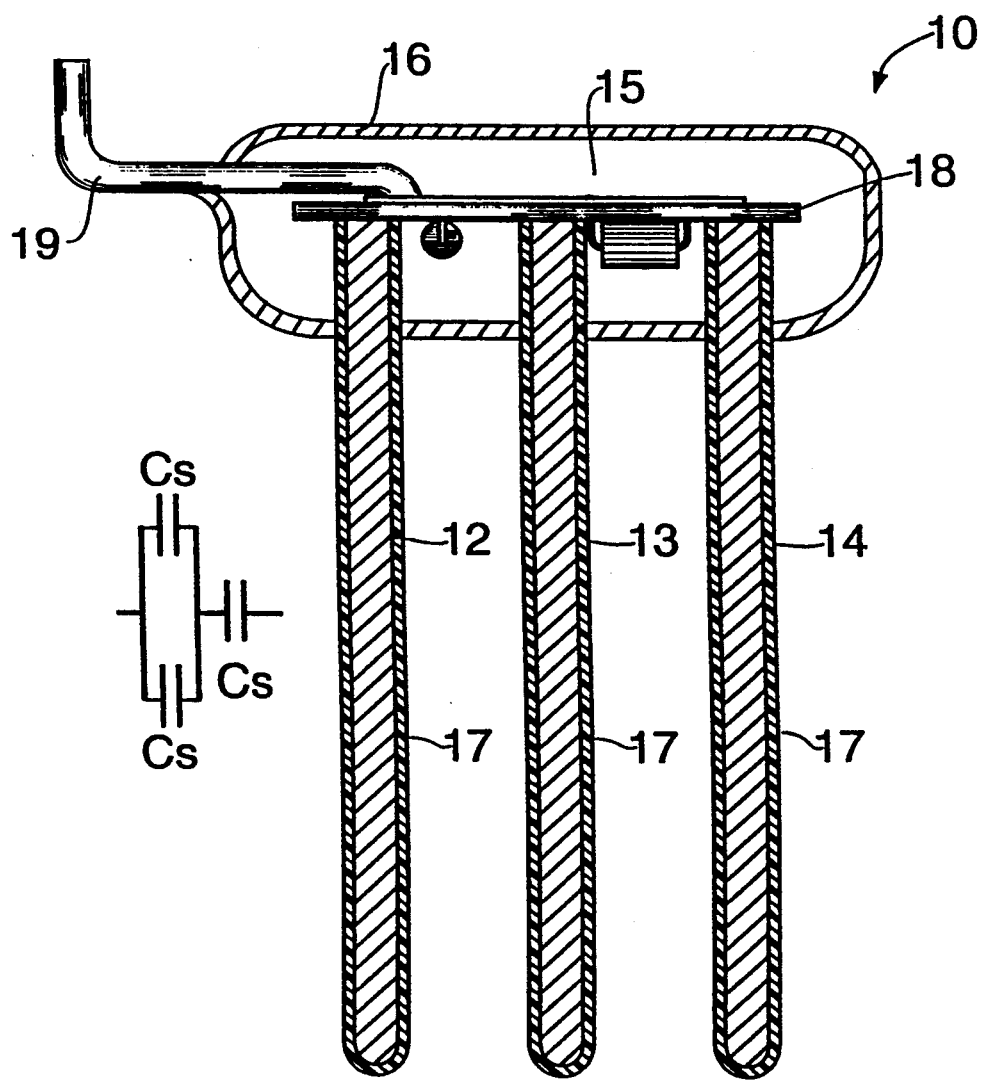
FIG. 5 is an alternative embodiment of the soil moisture sensor of FIGS. 1-3, featuring three electrodes.

In FIG. 5, there is shown an alternative embodiment of soil moisture sensor 10, featuring three electrodes 12, 13 and 14. The equivalent capacitance Cs of each of these electrodes may be connected as shown in the equivalent circuit representation, providing an increased sensitivity to soil moisture by increasing the effective conducting area 22, as defined in FIGS. 2-3.

Figure 6:
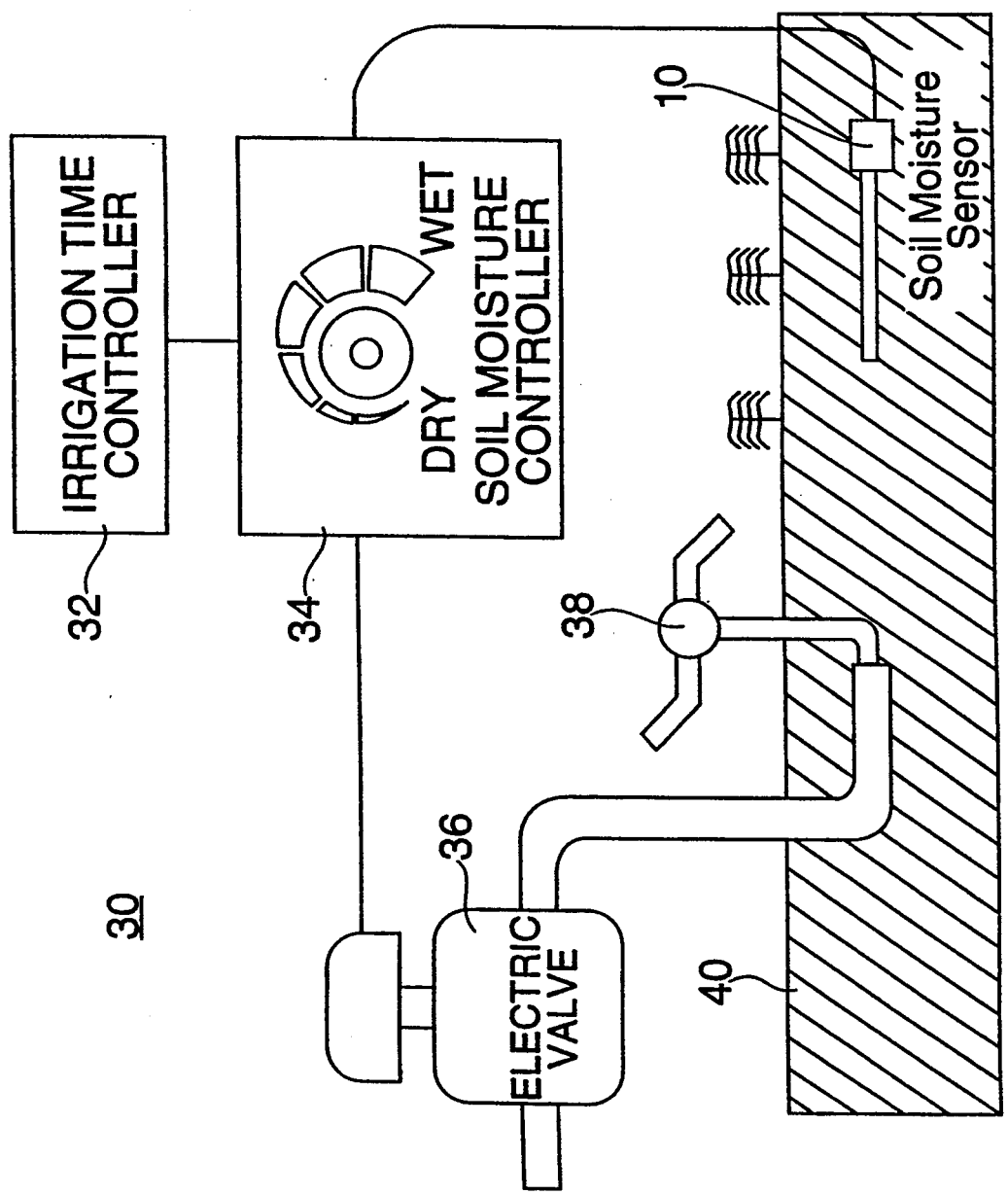
FIG. 6 is a schematic block diagram of an irrigation control system using the moisture sensor of FIGS. 1.

FIG. 6 a schematic block diagram of an irrigation control system 30 using moisture sensor 10 of FIGS. 1-3. Irrigation control system 30 comprises an irrigation time controller 32 and soil moisture controller 34 which receives data from moisture sensor 10. Typically, this configuration is used with existing control systems 30 already having a time controller 32, and soil moisture controller 34 is connected between the time controller 32 and an irrigation control valve 36. Control valve 36 controls the flow of water to a sprinkler system 38 for irrigating the ground 40 in which sensor 10 is buried. The operation of control system 30 is described further herein.

Figure 7:
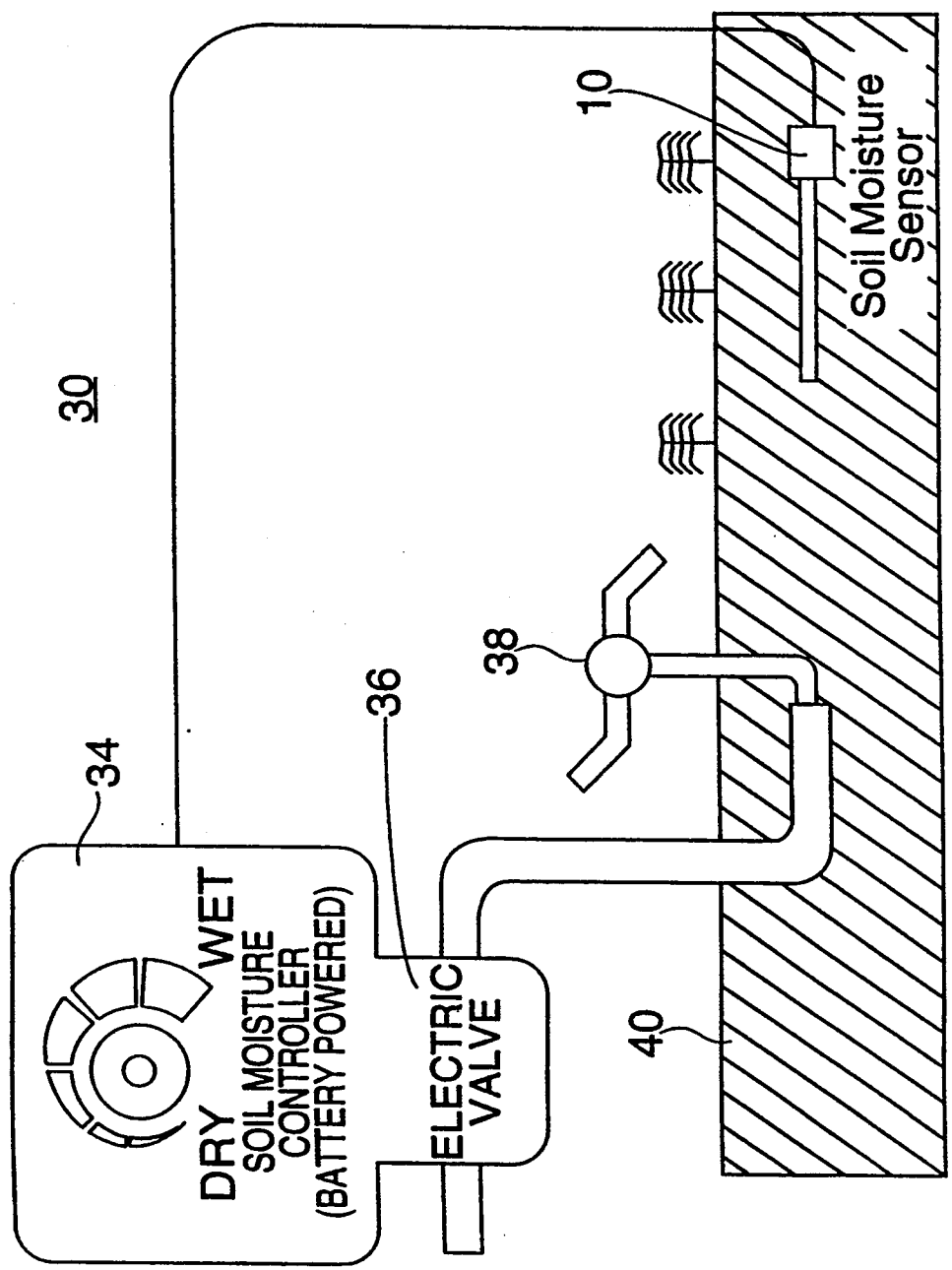
FIG. 7 is a schematic block diagram of an alternative irrigation control system using the moisture sensor of FIGS. 1.

In FIG. 7, an alternative arrangement of soil moisture control system 30 is shown, in which soil moisture controller 34 is integrally supplied as part of irrigation control valve 36. In this arrangement, control system 30 performs the irrigation based on a timer, and sensor 10 provides information on the soil moisture which is used to operate control valve 36.

The basic difference between the arrangements of FIGS. 6-7 is whether the soil moisture sensor 10 is sold as a separate device between a timer and a valve or whether it is sold as an integrated package in which the timer and valve and controller are all included as one.

Figure 8:
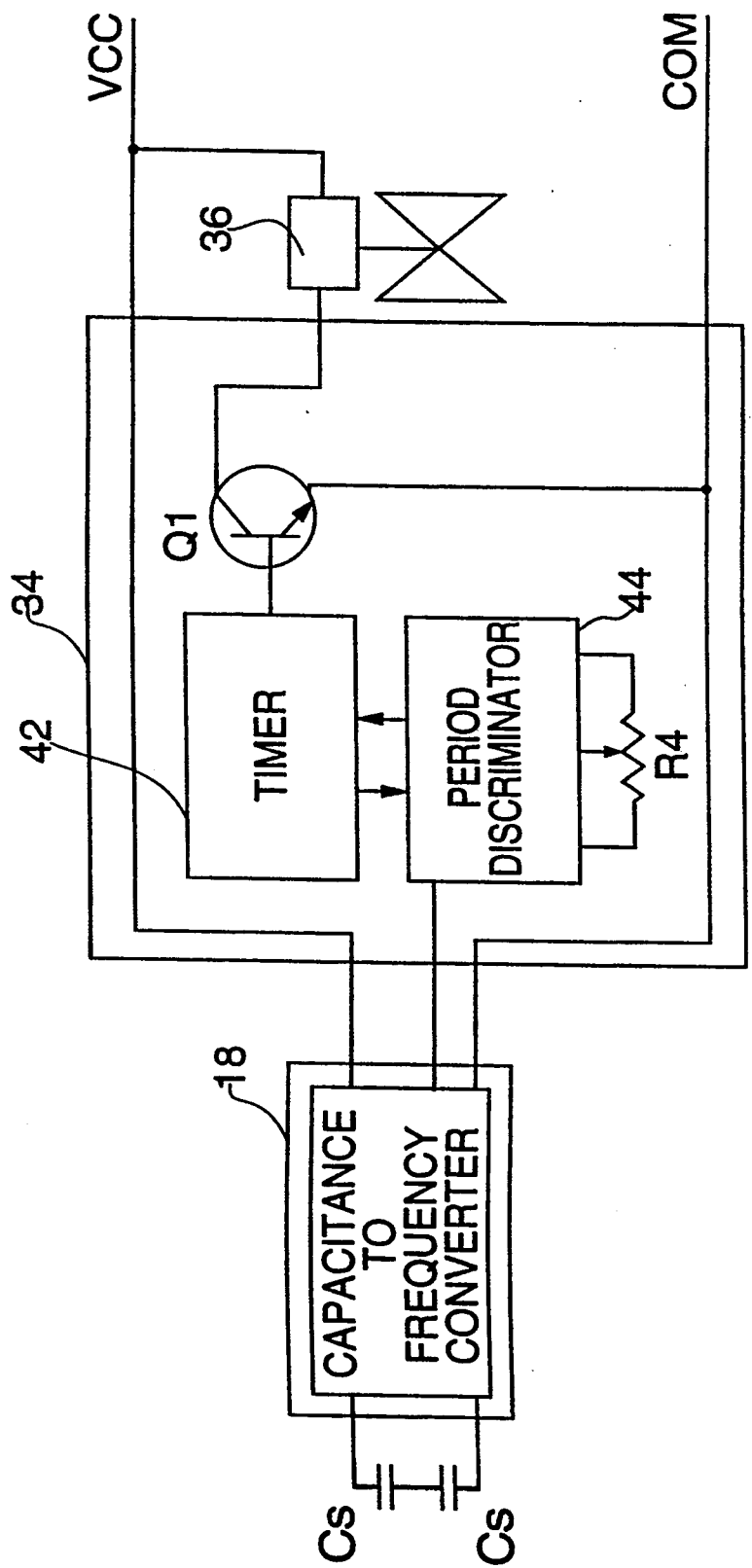
FIGS. 8-9 are, respectively, alternative electronic schematic diagrams of a soil moisture controller for use in the systems of FIGS. 6-7.
Figure 9:
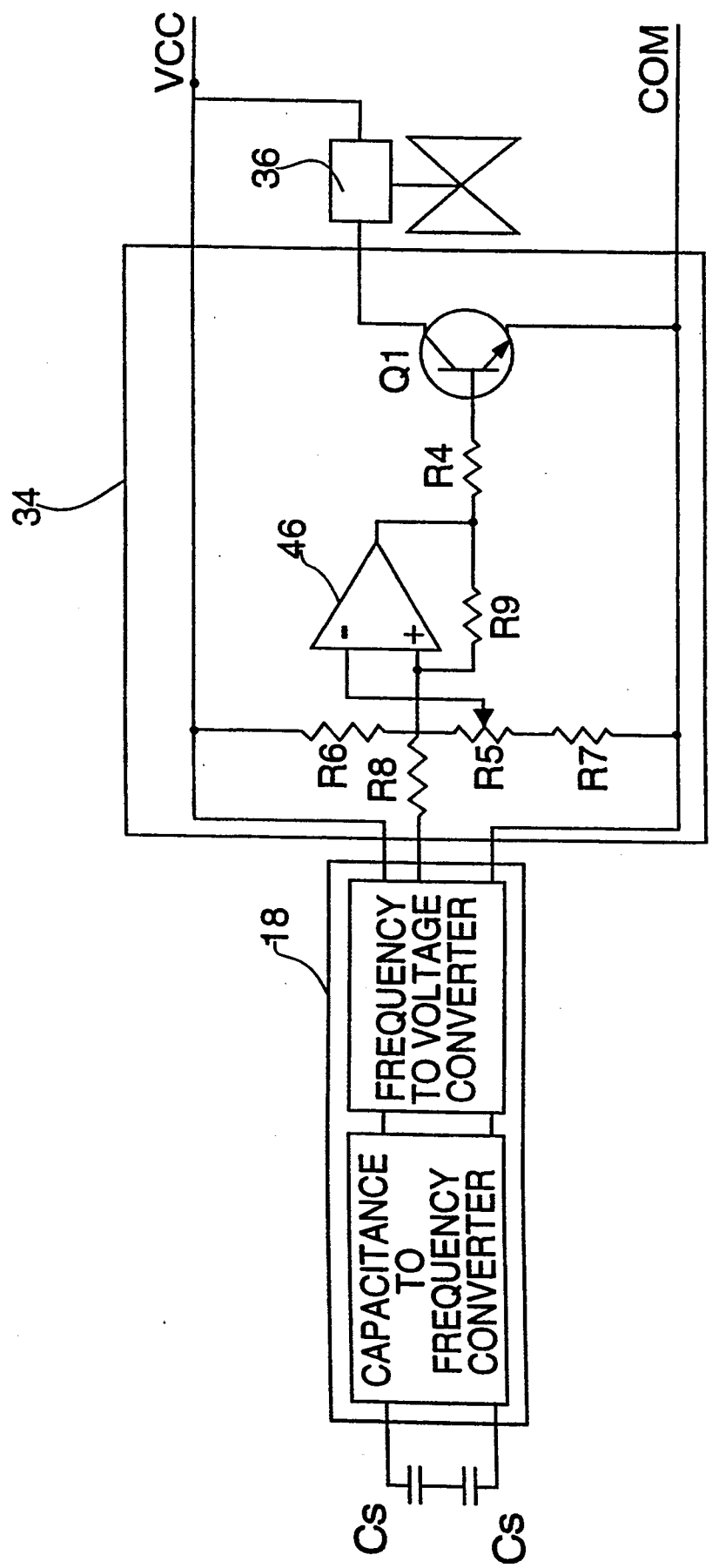

In FIGS. 8-9 there are shown, alternative electronic schematic block diagrams of a soil moisture controller 34 for use in the systems of FIGS. 6-7. In FIG. 8, soil moisture controller 34 is configured to operate based on a frequency input signal from conversion circuit 18. An internal timer 42 operates to divide an irrigation interval into subintervals, during which the system provides irrigation on a recurring basis.

When timer 42 determines that the time for irrigation has arrived normally, soil moisture controller 34 checks with soil moisture sensor 10 to determine whether the time should be used for irrigation, but if sufficient moisture is present, the system remains inactive. This determination is made by a discriminator 44, which examines the period (frequency) of the conversion circuit 18 output signal, representing soil moisture. A potentiometer R4 adjusts the threshold value for desired soil moisture, and timer 42 activates control valve 36 if the soil moisture falls below this predetermined threshold.

The operation of soil moisture controller 34 in this mode is based on the assumption that soil moisture changes slowly, and if it is too low, irrigation must be provided for an interval without checking the soil moisture again until the next time interval.

In FIG. 9, soil moisture controller 34 is configured to operate based on a voltage input signal from conversion circuit 18. In this arrangement, a voltage comparator is provided by operational amplifier 46, and its sensitivity is adjustable via adjustment of potentiometer R5, which operates in the voltage range established by the voltage divider provided by resistors R6-R7. When the soil moisture fails below a certain threshold, sensor 10 detects this, and at that point control valve 36 is operated. Thus, the soil moisture level is continuously monitored, and irrigation performed as required.

A "dead zone" in the sensitivity of the voltage comparator can be established by resistors R8-R9, so that an upper and a lower voltage threshold are defined to develop a voltage range in which control valve 36 will not be activated. Thus, irrigation is provided with a hysteresis function.

Figure 10:
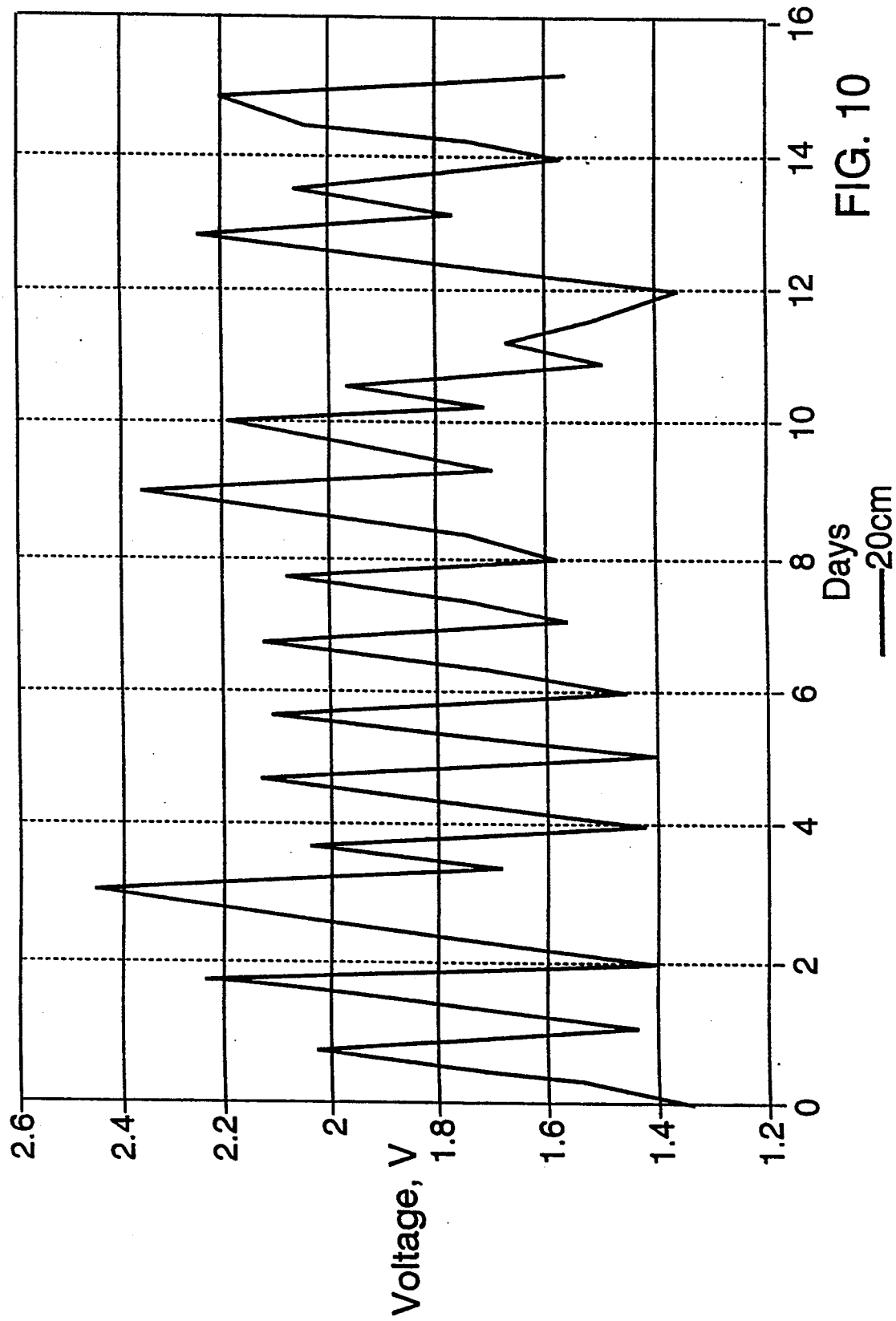
FIG. 10 is a graph showing soil moisture measurement fluctuations associated with prior art irrigation procedures.

FIGS. 10 and provide a comparison of the soil moisture measurement results obtained, in terms of voltage.

The comparison is between prior art irrigation methods which do not use soil moisture sensing and methods which use the inventive soil moisture sensor 10. In FIG. 10, the graph shows large soil moisture fluctuations associated with prior art irrigation procedures.

Figure 11:
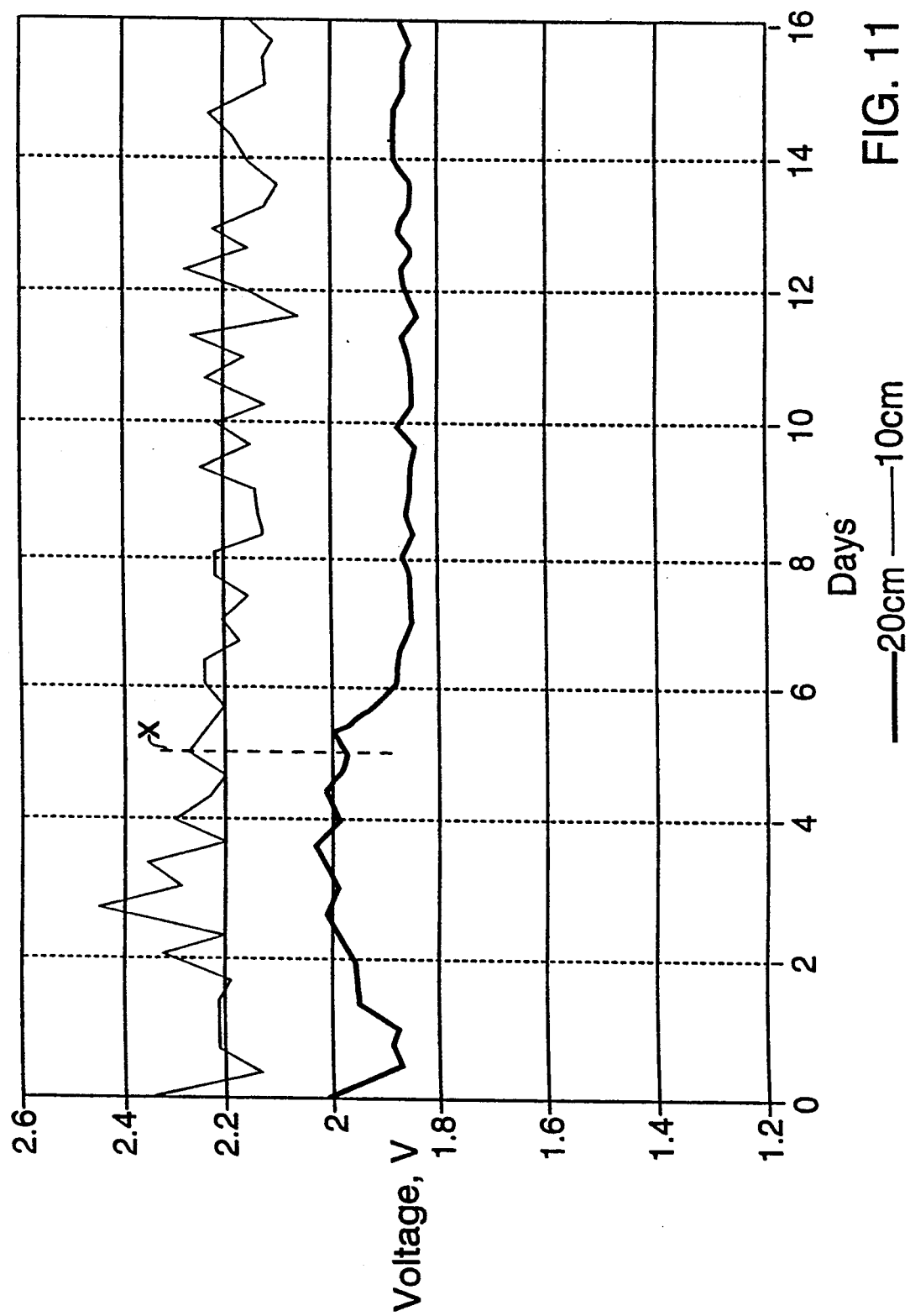
FIG. 11 is a graph showing soil moisture measurements with irrigation systems using the inventive soil moisture sensor.

In FIG. 11, there is shown a graph of soil moisture measurements obtained with irrigation systems using the inventive soil moisture sensor 10, based on operation with a hysteresis function. A moisture sensor 10 controlling the valve was buried at 10 cm in the soil, and a second moisture sensor 10 was buried at 20 cm for comparison. As can be readily seen, the fluctuations in soil moisture are small and the desired level of soil moisture can be maintained over time and at the desired soil depth. In addition, control valve 36 can be operated to effect a change to a different level of soil moisture, such as that appearing on day five (point X), and this is achieved with minimum disturbances.

Figure 12:
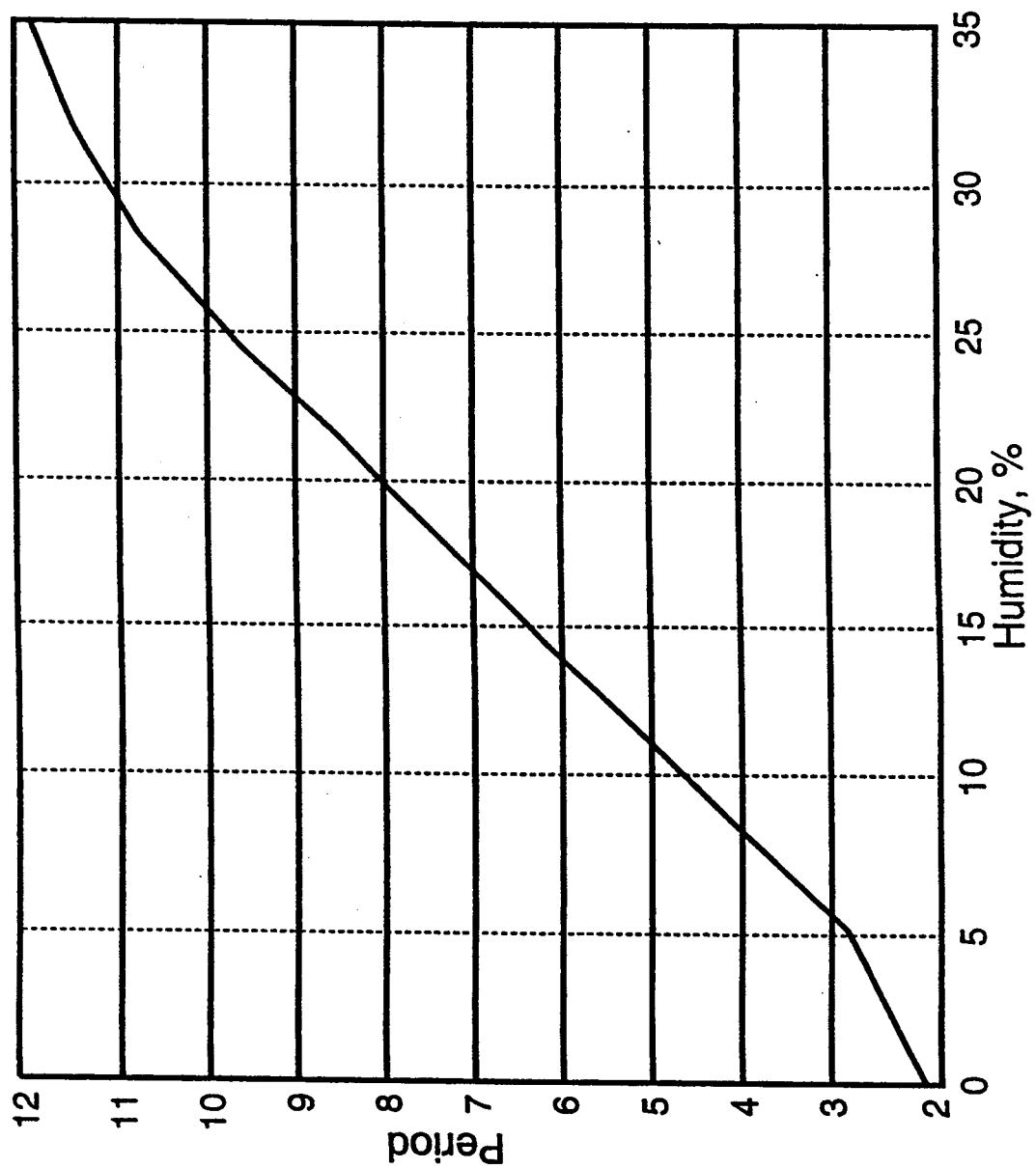
FIG. 12 is a graph showing the relationship of soil moisture to a parameter of the inventive soil moisture sensor.

FIG. 12 is a graph showing the relationship between soil moisture and the system parameter defined as the period (frequency) which can be derived through the circuitry previously described. It can be observed that there is a linear relationship between the moisture and the period. The linear relationship increases the accuracy and reliability of soil moisture sensor 10 measurements.

Figure 13A:
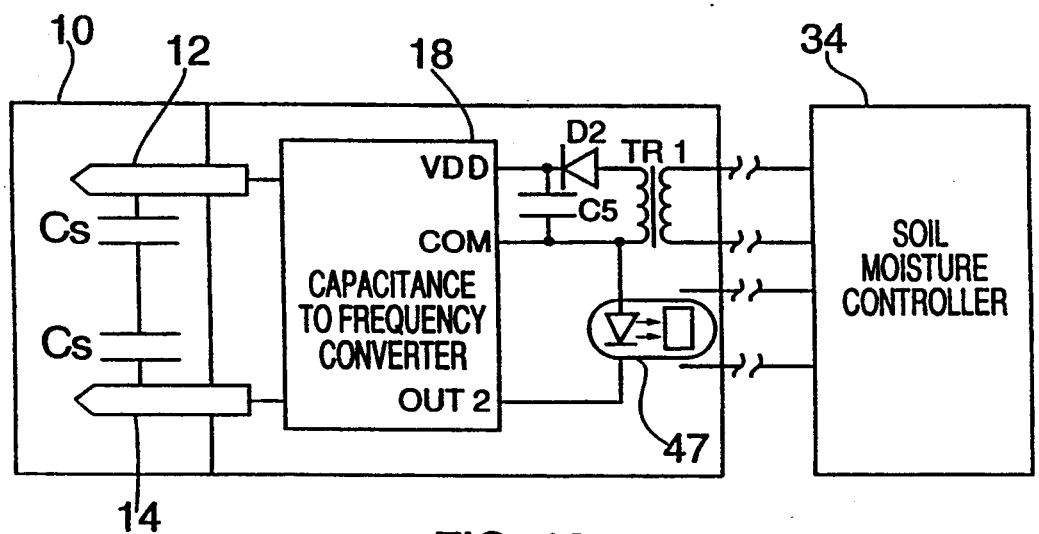
FIGS. 13a-b are schematic diagrams of the soil moisture sensor using an isolation transformer to increase accuracy.
Figure 13B:
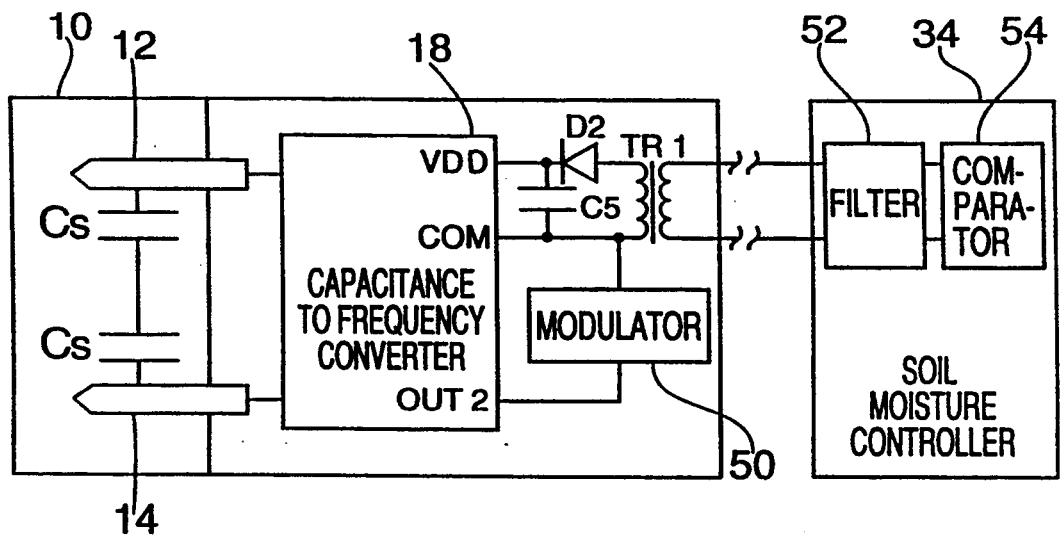

Referring now to FIGS. 13a–b, there are shown schematic diagrams of alternative soil moisture sensor 10 embodiments designed to increase the measurement accuracy by minimizing the undesirable effects of parasitic capacitance. For example, in FIG. 4, each of isolation capacitors C1 and C2 will act as a short circuit at high frequency, and thus the COM line will be effectively connected to the electrode 14. Similarly, the supply voltage Vdd and output signal OUT2 will be effectively connected to electrode 12. As a result, the soil moisture surrounding the external cable connections between conversion circuit 18 and soil moisture controller 34 develop a parasitic capacitance, which is especially problematic for measurement accuracy where large distances separate sensor 10 and soil moisture controller 34.

FIG. 13a shows a solution to this problem by the addition of isolation transformer TR1 to conversion circuit 18. Soil moisture controller 34 supplies AC voltage, via isolation transformer TR1, which is rectified by diode D2 and capacitor C5. An optocoupler 47 connected between output terminal OUT2 and the COM line provides electrical isolation between output signal OUT2 and the external connections to soil moisture controller 34.

In FIG. 13b, another alternative embodiment of sensor 10 is shown, in which output signal OUT2 is fed to modulator 50 so that the voltage supplied to isolation transformer TR1 is modulated by this signal. A filter 52 and comparator 54 are provided in soil moisture controller 34 to demodulate and reconstruct signal OUT2 for use in soil moisture controller 34. This arrangement reduces the cost of sensor 10 and system 30.

Having described the invention with regard to certain specific embodiments, it is to be understood that the description is not meant as a limitation since further modifications may now suggest themselves to those skilled in the art and it is intended to cover such modifications as fall within the scope of the appended claims.

We claim:

1. A soil moisture sensor comprising:

at least a pair of rod-shaped electrodes being spaced apart from one another by a relatively large distance in relation to their diameters, each of said electrodes being disposed in the earth and having a thin dielectric coating each said electrode defining a first plate of a capacitor, said thin dielectric coating being in contact over an area thereof with a plurality of soil particles containing moisture to define a second plate of each of said capacitors over said contact area, said pair of electrodes each providing a capacitor having a relatively high capacitance, said pair of capacitors being connected serially through conductivity of said soil particles containing moisture, and variable frequency oscillator means coupled to said capacitors and providing an output frequency responsive to a sensed capacitance, wherein said sensed capacitance is related to an effective conducting area defined by said contact area between said thin dielectric coating and said moisture contained by said plurality of soil particles.

2. The sensor of claim 1 wherein said sensed capacitance comprises an equivalent capacitance of a pair of capacitors being connected serially, wherein each of said pair capacitors is provided by a parallel connection of a plurality of dielectric-coated electrodes each providing a capacitor.

3. The sensor of claim 1 wherein a set of three of said dielectric-coated electrodes is longitudinally disposed in a common plane, two of said electrodes each being disposed on either side of a middle electrode, said two electrodes defining capacitors being connected in parallel, said middle electrode defining a capacitor being connected in series with said two parallel-connected capacitors.

4. The sensor of claim 1 wherein each of said electrodes is connected to an isolation capacitor for reducing the undesired effect of damage to said thin dielectric coating.

5. The sensor of claim 1 wherein said electrode is arranged to measure a liquid height, said effective conducting area extending over a length of said electrode and said sensed capacitance being continually monitored over said electrode length to provide a level sensor of said liquid height.

6. The sensor of claim 1 wherein said output frequency is provided to a control valve in an irrigation system to control operation thereof in response to a predetermined frequency level.

7. The sensor of claim 1 wherein said output frequency is converted to a voltage by a frequency-to-voltage converter.

8. The sensor of claim 7 wherein said voltage is provided to a control valve in an irrigation system to control operation thereof in response to a predetermined voltage level.

9. The sensor of claim 1 wherein said output frequency provided for use in an irrigation system via a set of external connections between said sensor and a control device, said external connections being electrically isolated from said sensor electrodes.

10. The sensor of claim 9 wherein said external connections are electrically isolated by an isolation transformer.

11. The sensor of claim 9 wherein said external connections are electrically isolated by an optocoupler.

12. A method of measuring soil moisture comprising the steps of:

providing at least a pair of rod-shaped electrodes, being spaced apart from each other by a relatively large distance in relation to their diameters, each of said electrodes being disposed in the earth and having a thin dielectric coating, each said electrode defining a first plate of a capacitor, said thin dielectric coating being in contact over an area thereof with a plurality of soil particles containing moisture to define a second plate of each of said capacitors over said contact area, said pair of electrodes each providing a capacitor having a relatively high capacitance, said pair of capacitors being connected serially through conductivity of said soil particles containing moisture;

sensing a capacitance developed between said first plate and said contact area of each electrode; and providing an output frequency responsive to said sensed capacitance, wherein said sensed capacitance is related to an effective conducting area defined by said contact area between said thin dielectric coating, and said moisture contained by said plurality of soil particles.

13. The method of claim 12 further comprising a plurality of additional rod-shaped electrodes each having said thin dielectric coating and being disposed in the soil to define a plurality of capacitors providing a capacitance in addition to said sensed capacitance.

14. The method of claim 12 wherein said sensed capacitance is continually monitored to provide a soil moisture measurement.

15. The method of claim 12 wherein said output frequency is provided to a control valve in an irrigation system to control operation thereof in response to a predetermined frequency level.

16. The method of claim 12 wherein said output frequency is converted to a voltage by a frequency-to-voltage converter.

17. The method of claim 16 wherein said voltage is provided to a control valve in an irrigation system to control operation thereof in response to a predetermined voltage level.

18. The method of claim 12 wherein said output frequency is provided for use in an irrigation system via a set of external connections electrically isolated from said electrode,

* * * * *